(12) United States Patent
Kai et al.

(10) Patent No.: US 8,703,302 B2
(45) Date of Patent: Apr. 22, 2014

(54) INDOLOCARBAZOLE DERIVATIVE WITH AROMATIC PHOSPHNE OXIDE GROUP FOR ORGANIC ELECTROLUMINESCENT DEVICE AND ORGANIC ELECTROLUMINESCENT DEVICE CONTAINING SAME

(75) Inventors: Takahiro Kai, Kitakyushu (JP); Masaki Komori, Kitakyushu (JP); Toshihiro Yamamoto, Katakyushu (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 213 days.

(21) Appl. No.: 12/991,167

(22) PCT Filed: Apr. 30, 2009

(86) PCT No.: PCT/JP2009/058451
§ 371 (c)(1),
(2), (4) Date: Nov. 5, 2010

(87) PCT Pub. No.: WO2009/136586
PCT Pub. Date: Nov. 12, 2009

(65) Prior Publication Data
US 2011/0057184 A1    Mar. 10, 2011

(30) Foreign Application Priority Data
May 8, 2008   (JP) .................................. 2008-122060

(51) Int. Cl.
*H01L 51/54* (2006.01)
*C09K 11/06* (2006.01)
*C07F 9/6561* (2006.01)

(52) U.S. Cl.
USPC ............. 428/690; 428/917; 548/414; 257/40; 257/E51.049

(58) Field of Classification Search
None
See application file for complete search history.

(56) References Cited

U.S. PATENT DOCUMENTS

| | | | |
|---|---|---|---|
| 5,942,340 A | 8/1999 | Hu et al. | |
| 5,952,115 A | 9/1999 | Hu et al. | |
| 2008/0220285 A1 * | 9/2008 | Vestweber et al. | ............ 428/690 |
| 2009/0295276 A1 | 12/2009 | Asari et al. | |

FOREIGN PATENT DOCUMENTS

| | | |
|---|---|---|
| JP | 11-144866 A | 5/1999 |
| JP | 11-162650 A | 6/1999 |
| JP | 11-176578 A | 7/1999 |
| JP | 2007-109988 A | 4/2007 |
| WO | WO 2007/063796 A1 | 6/2007 |

OTHER PUBLICATIONS

Cai et al. "Electron and hole transport in a wide bandgap organic phosphine oxide for blue electrophosphorescence" Applied Physics Letters 2008, 92, 083308-1-083308-3. Date of publication: Feb. 28, 2008.*
International Preliminary Report on Patentability (in English) and Written Opinion of the International Search Authority (Japanese language version), mailed Nov. 18, 2010, for International Application No. PCT/JP2009/058451 (Forms PCT/IB/326, PCT/IB/373 and PCT/ISA/237).
International Search Report, dated Aug. 18, 2009, for International Application No. PCT/JP2009/058451.
Sapochak et al., "Inductive Effects of Diphenylphosphoryl Moieties on Carbazole Host Materials: Design Rules for Blue Electrophosphorescent Organic Light-Emitting Devices," J. Phys. Chem. C, vol. 112, 2008, pp. 7989-7996.
Notification of Transmittal of Translation of the International Preliminary Report on Patentability and English translation of the International Preliminary Report on Patentability dated Dec. 23, 2010 (Forms PCT/IB/338 and PCT/IB/373).
Written Opinion of the International Searching Authority dated Aug. 18, 2009 for Application No. PCT/JP2009/058451 (Form PCT/ISA/237).

* cited by examiner

*Primary Examiner* — Andrew K Bohaty
(74) *Attorney, Agent, or Firm* — Birch, Stewart, Kolasch & Birch, LLP

(57) ABSTRACT

Disclosed is an organic electroluminescent device (organic EL device) that is improved in the luminous efficiency, fully secured of the driving stability, and of a simple structure and disclosed also is a compound useful therefor. The organic EL device comprises a light-emitting layer disposed between an anode and a cathode piled one upon another on a substrate and the said light-emitting layer comprises a phosphorescent dopant and an indolocarbazole derivative as a host material. The indolocarbazole derivative is represented by the following formula (3) wherein Ar is an aromatic group and L is a direct bond or an aromatic group.

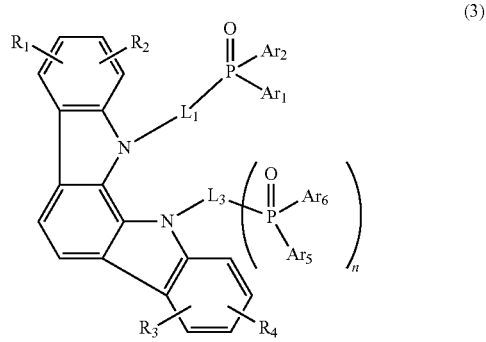

(3)

8 Claims, 1 Drawing Sheet

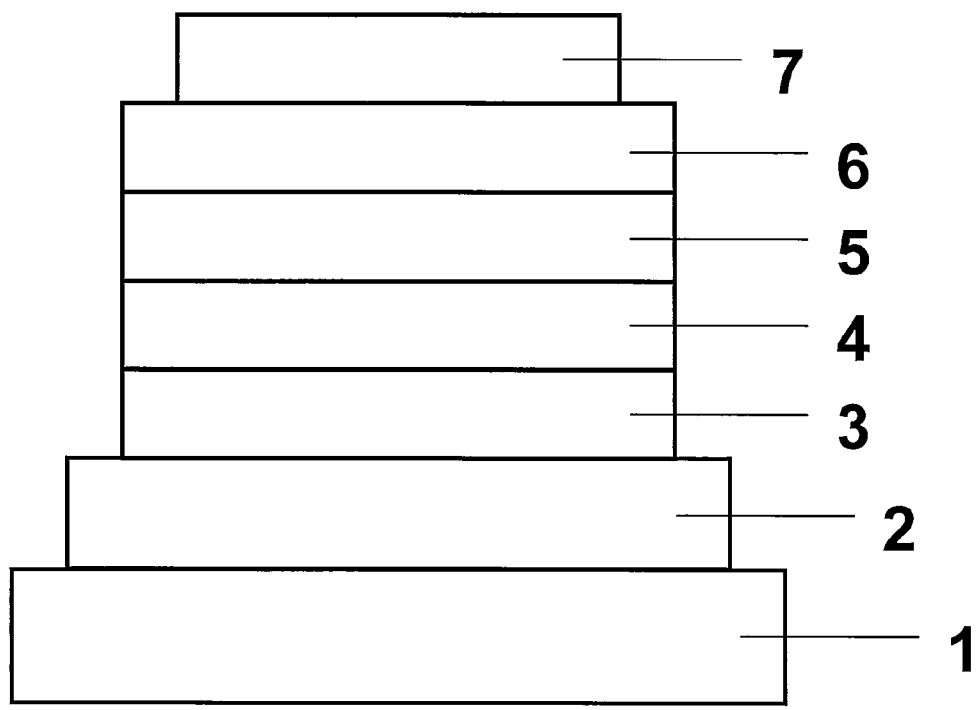

INDOLOCARBAZOLE DERIVATIVE WITH AROMATIC PHOSPHNE OXIDE GROUP FOR ORGANIC ELECTROLUMINESCENT DEVICE AND ORGANIC ELECTROLUMINESCENT DEVICE CONTAINING SAME

FIELD OF TECHNOLOGY

This invention relates to a novel compound for organic electroluminescent device and to an organic electroluminescent device (hereinafter referred to as organic EL device) using the said novel compound.

BACKGROUND TECHNOLOGY

An organic electroluminescent device in the simplest structure is generally constituted of a light-emitting layer and a pair of counter electrodes sandwiching the said light-emitting layer. The device functions by utilizing the following phenomenon; upon application of an electrical field between the electrodes, electrons are injected from the cathode and holes are injected from the anode and they recombine in the light-emitting layer with emission of light.

In recent years, organic thin films have been used in the development of organic EL devices. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been directed toward commercial applications to high-performance flat panels featuring self-luminescence and high-speed response.

In another effort to enhance the luminous efficiency of the device, the use of phosphorescence in place of fluorescence is investigated. The aforementioned device comprising a hole-transporting layer composed of an aromatic amine and a light-emitting layer composed of Alq3 and many other devices utilize fluorescence. The use of phosphorescence, that is, emission of light from the excited triplet state, is expected to enhance the luminous efficiency three to four times that of the conventional devices utilizing fluorescence (emission of light from the excited singlet state). To achieve this objective, the use of coumarin derivatives and benzophenone derivatives in the light-emitting layer was investigated, but these derivatives merely produced luminance at an extremely low level. Europium complexes were also investigated in trials to utilize the excited triplet state, but they failed to emit light at high efficiency. In recent years, as is mentioned in patent document 1, a large number of researches are conducted with the objective of enhancing the luminous efficiency and extending the lifetime while giving priority to utilization of organic metal complexes such as iridium complexes.

Patent document 1: JP2003-515897 A
Patent document 2: JP2001-313178 A
Patent document 3: JP2002-352957 A
Patent document 4: JP H11-162650A
Patent document 5: JP H11-176578A
Patent document 6: WO2007/063796
Patent document 7: JP2007-129206 A
Patent document 8: WO2007/137725

In order to enhance the luminous efficiency by utilizing phosphorescence, a host material to be used together with a dopant material becomes important. Of the host materials proposed thus far, a typical example is 4,4'-bis(9-carbazolyl)biphenyl (hereinafter referred to as CBP), a carbazole compound cited in patent document 2. When CBP is used as a host material for tris(2-phenylpyridine)iridium complex (hereinafter referred to as Ir(ppy)3), a phosphorescent material emitting green light, the balance of electrical charges in the light-emitting layer is destroyed and excess holes flow out to the side of the cathode on account of the electron transport property being inferior to the hole transport property in the case of CBP and the result is lowering of the luminous efficiency due to lowering of the recombination probability in the light-emitting layer. Furthermore, in this case, the recombination zone in the light-emitting layer is limited to a narrow space in the vicinity of the interface on the cathode side. Consequently, in the case where an electron-transporting material, such as Alq3, whose lowest triplet energy level is lower than that of Ir(ppy)3 is used, there may arise a possibility that the luminous efficiency becomes lower due to transfer of the triplet energy from the dopant to the electron-transporting material.

On the other hand, 3-phenyl-4-(1'-naphthyl)-5-phenyl-1,2,4-triazole (hereinafter referred to as TAZ), disclosed in patent document 3, is also proposed as a host material for a phosphorescent organic EL device. As the hole transport property is inferior to the electron transport property in the case of TAZ, the light-emitting zone is on the side of the hole-transporting layer. In this case, the chosen hole-transporting material influences the luminous efficiency of Ir(ppy)3. For example, the use of 4,4'-bis[N-(1-naphthyl)-N-phenylamino]biphenyl (hereinafter referred to as NPB), a material in widespread use for its good performance, high reliability, and long lifetime, in the hole-transporting layer causes a problem that the triplet energy is transferred from Ir(ppy)3 to NPB reflecting the relationship of the lowest triplet energy level between the two and the luminous efficiency becomes lower.

Furthermore, compounds like CBP and TAZ readily undergo crystallization and agglomeration with the resultant deterioration of the shape of thin film. In addition, the Tg of such compounds is difficult to merely observe because of their high crystallinity. The instability of the shape of thin film in the light-emitting layer exerts an adverse influence on the device such as shortening of the lifetime and lowering of the heat resistance.

As the aforementioned examples indicate, it can readily be understood that a demand is created for host materials that possess simultaneously a high hole transport property and a high electron transport property and are well balanced in the electrical charges (hole and electron) transport properties. Furthermore, it is desirable that the host materials are endowed with electrochemical stability, high heat resistance, and good stability in the amorphous state.

Further, although patent documents 4, 5, and 6 disclose the use of a certain kind of indolocarbazole compounds in organic EL devices and patent documents 7 and 8 likewise disclose the use of a certain kind of phosphorus oxides in organic EL devices, there is a demand for compounds of better properties that are suitable for use in organic EL devices.

DISCLOSURE OF THE INVENTION

In applications of organic EL devices to display devices such as flat panel displays, it is necessary to enhance the luminous efficiency of the device and, at the same time, to fully secure the driving stability of the device. Under the aforementioned circumstances, an object of this invention is to provide an organic EL device of high efficiency, good driving stability, and practical usefulness and to provide a compound suitable therefor.

The inventors of this invention have conducted intensive studies, found as a result that the use of compounds of a specified structure in organic EL devices can solve the aforementioned problems, and completed this invention.

Accordingly, this invention relates to an organic EL device using a compound of a specified indolocarbazole skeleton.

A compound for organic electroluminescent device according to this invention is represented by the following general formula (1).

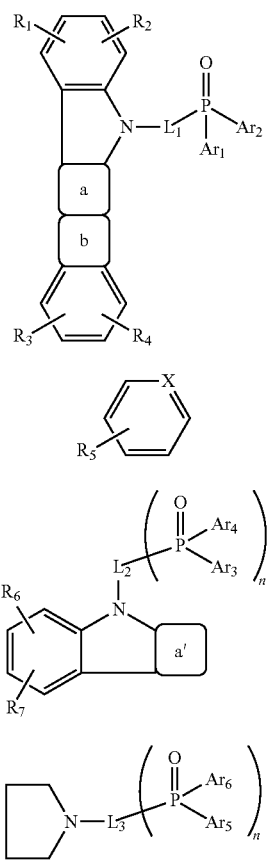

In general formula (1), ring a is an aromatic or heterocyclic ring fused to two adjacent rings and represented by formula (a1) or (a2), ring a' is an aromatic or heterocyclic ring fused to three adjacent rings and represented by formula (a1), and ring b is a heterocyclic ring fused to two adjacent rings and represented by formula (b1); X is independently CR or N; $Ar_1$ to $Ar_6$ each is independently a substituted or unsubstituted aromatic hydrocarbon or aromatic heterocyclic group; R and $R_1$ to $R_7$ each is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, or a substituted or unsubstituted aromatic hydrocarbon or aromatic heterocyclic group and in the case where any two of the foregoing are located adjacent to each other, they may be linked to form a fused ring; $L_1$ to $L_3$ each is independently a direct bond or a linking group constituted of a substituted or unsubstituted aromatic hydrocarbon or aromatic heterocyclic group; n is an integer of 0 or 1.

The compounds for organic electroluminescent devices represented by general formula (1) include compounds represented by the following general formula (2) and the compounds represented by general formula (2) include compounds represented by the following general formula (3).

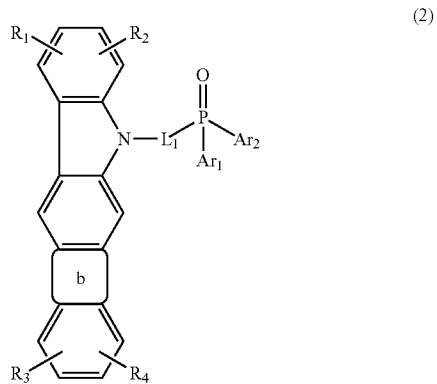

In general formula (2), ring b, $Ar_1$, $Ar_2$, $Ar_5$, $Ar_6$, $R_1$ to $R_4$, $L_1$, and $L_3$ respectively have the same meaning as ring b, $Ar_1$, $Ar_2$, $Ar_5$, $Ar_6$, $R_1$ to $R_4$, $L_1$, and $L_3$ in general formula (1).

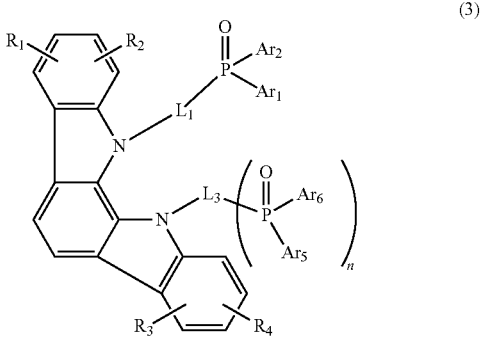

In formula (3), $Ar_1$, $Ar_2$, $Ar_5$, $Ar_6$, $R_1$ to $R_4$, $L_1$, $L_3$, and n respectively have the same meaning as $Ar_1$, $Ar_2$, $Ar_5$, $Ar_6$, $R_1$ to $R_4$, $L_1$, $L_3$, and n in general formula (1).

Further, this invention relates to an organic electroluminescent device that comprises an organic layer comprising the aforementioned compound for organic electroluminescent device. Advantageously, the said organic layer is at least one layer selected from a light-emitting layer, a hole-transporting layer, a hole-injecting layer, an electron-transporting layer, an electron-injecting layer, and a hole-blocking layer. More advantageously, this invention relates to an organic electroluminescent device in which the said light-emitting layer comprises a phosphorescent dopant and a compound for organic electroluminescent device represented by the aforementioned general formula (1), (2), or (3).

BRIEF DESCRIPTION OF THE DRAWING

FIG. 1 shows the cross section of an example of an organic EL device.

PREFERRED EMBODIMENTS OF THE INVENTION

The compounds for organic EL device of this invention are represented by the aforementioned general formula (1). Of these compounds, the preferred ones include the compounds represented by the aforementioned general formula (2). Furthermore, of the compounds represented by general formula (2), the preferred ones include the compounds represented by the aforementioned general formula (3). A compound represented by general formula (1) typically possesses an indolocarbazole skeleton formed by fusion of a carbazole ring and an indole ring. The N atom in the carbazole ring is linked directly or through a linking group to P=O and the P=O is further linked to two Ars.

In general formula (1), ring a is an aromatic or heterocyclic ring fused to two adjacent rings and represented by formula (a1) or (a2). In the case where ring a is a heterocyclic ring represented by formula (a2), ring a' is fused to the adjacent ring. Ring a' is an aromatic or heterocyclic ring represented by formula (a1). In formula (a1), X is CR or N. Here, R is a group similar to $R_1$ to $R_7$ and it is preferably hydrogen.

Ring b is a heterocyclic ring fused to two adjacent rings and represented by formula (b1). The structure of general formula (1) changes into the structure of general formula (2) when ring a is specified or into the structure of general formula (3) when ring a and ring b are specified. Further, the symbols used in general formula (1) have the same meaning in general formulas (2) and (3). Hence, general formulas (2) and (3) can be understood by explanation of general formula (1).

In general formula (1) and formulas (a1) and (a2), $Ar_1$ to $Ar_6$ each is a substituted or unsubstituted aromatic hydrocarbon group or a substituted or unsubstituted aromatic heterocyclic group.

Preferable examples of the unsubstituted aromatic hydrocarbon groups include the monovalent groups formed by removing one hydrogen atom from benzene, naphthalene, anthracene, phenanthrene, indene, and the like and a phenyl group and a naphthyl group are more preferable.

Preferable examples of the unsubstituted aromatic heterocyclic groups include the monovalent groups formed by removing one hydrogen atom from thiophene, thiazole, furan, oxazole, pyran, pyrrole, imidazole, pyrazole, isothiazole, isoxazole, frazan, triazole, pyridine, pyrazine, pyrimidine, pyridazine, triazine, benzothiophene, benzothiazole, thianthrene, isobenzofuran, benzoxazole, chromene, xanthene, phenoxathiin, indolizine, isoindole, indole, benzimidazole, indazole, benzotriazole, purine, quinolizine, isoquinoline, quinoline, phthalazine, naphthyridine, quinoxaline, quinazoline, cinnoline, pterizine, carbazole, carboline, phenanthridine, acridine, perimidine, phenanthroline, phenazine, phenothiazine, phenoxazine, and dibenzodioxin. More preferable are the monovalent groups formed by removing one hydrogen atom from pyridine, pyrazine, pyrimidine, pyridazine, and triazine.

The groups $L_1$ to $L_3$ each is independently a direct bond, a divalent linking group constituted of a substituted or unsubstituted aromatic hydrocarbon or aromatic heterocyclic group, or a monovalent group constituted of a substituted or unsubstituted aromatic hydrocarbon or aromatic heterocyclic group. In the case where n is 0, $L_2$ or $L_3$ is a monovalent group; in other cases, $L_2$, $L_3$, and $L_1$ are divalent linking groups.

Preferable examples of the unsubstituted aromatic hydrocarbon groups include the monovalent or divalent groups formed by removing one or two hydrogen atoms from benzene, naphthalene, anthracene, phenanthrene, indene, biphenyl, terphenyl, and quaterphenyl. More preferable are the monovalent or divalent groups formed by removing one or two hydrogen atoms from benzene, biphenyl, and terphenyl.

Preferable examples of the unsubstituted aromatic heterocyclic groups include the monovalent or divalent groups formed by removing one or two hydrogen atoms from thiophene, thiazole, furan, oxazole, pyran, pyrrole, imidazole, pyrazole, isothiazole, isoxazole, frazan, triazole, pyridine, pyrazine, pyrimidine, pyridazine, triazine, benzothiophene, benzothiazole, thianthrene, isobenzofuran, benzoxazole, chromene, xanthene, phenoxathiin, indolizine, isoindole, indole, benzimidazole, indazole, benzotriazole, purine, quinolizine, isoquinoline, quinoline, phthalazine, naphthyridine, quinoxaline, quinazoline, cinnoline, pterizine, carbazole, carboline, phenanthridine, acridine, perimidine, phenanthroline, phenazine, phenothiazine, phenoxazine, and dibenzodioxin. More preferable are the monovalent or divalent groups formed by removing one or two hydrogen atoms from pyridine, pyrazine, pyrimidine, pyridazine, and triazine.

The groups $R_1$ to $R_7$ each is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, or a substituted or unsubstituted aromatic hydrocarbon or aromatic heterocyclic group. In the case where any two of the foregoing are located adjacent to each other, they may be linked to form a fused ring.

In the case where $R_1$ to $R_7$ each is an alkyl group, the number of carbon atoms in the alkyl group is preferably 1 to 6. In other cases, the preferable numbers of carbon atoms are as follows: 2 to 6 in the case of an alkenyl or alkynyl group, 7 to 13 in the case of an aralkyl group, 3 to 15 in the case of a substituted or unsubstituted aromatic hydrocarbon or aromatic heterocyclic group, 2 to 10 in the case of a dialkylamino group, 6 to 20 in the case of a diarylamino or diaralkylamino group, 2 to 10 in the case of an acyl or alkoxycarbonyl group, and 1 to 6 in the case of an alkoxyl, alkylsulfonyl, or haloalkyl group.

In the case where the aforementioned groups $Ar_1$ to $Ar_6$, $L_1$ to $L_3$, and $R_1$ to $R_7$ are aromatic hydrocarbon or aromatic heterocyclic groups carrying substituents, preferable substituents include an alkyl group of 1 to 6 carbon atoms, an alkoxyl group of 1 to 6 carbon atoms, an aryloxy group of 6 to 12 carbon atoms, an alkylthio group, a substituted amino group, an acetyl group, a phenyl group, a biphenylyl group, a terphenylyl group, a naphthyl group, a pyridyl group, a pyrimidyl group, a triazyl group, an imidazolyl group, a thienyl group, and a carbazolyl group.

Of the compounds represented by the aforementioned general formula (1), those which are preferred are represented by the aforementioned general formulas (2) and (3). Since the concept here is that the compounds represented by general formula (1) include the compounds represented by general formulas (2) and (3), the former will represent the latter in explanation in some cases.

The compounds for organic EL device of this invention can be prepared easily by one of known methods. For example, a compound represented by general formula (1) can be prepared by a sequence of reactions illustrated below with reference to a synthetic example described in Synlett., 2005, No. 1, pp. 42-48.

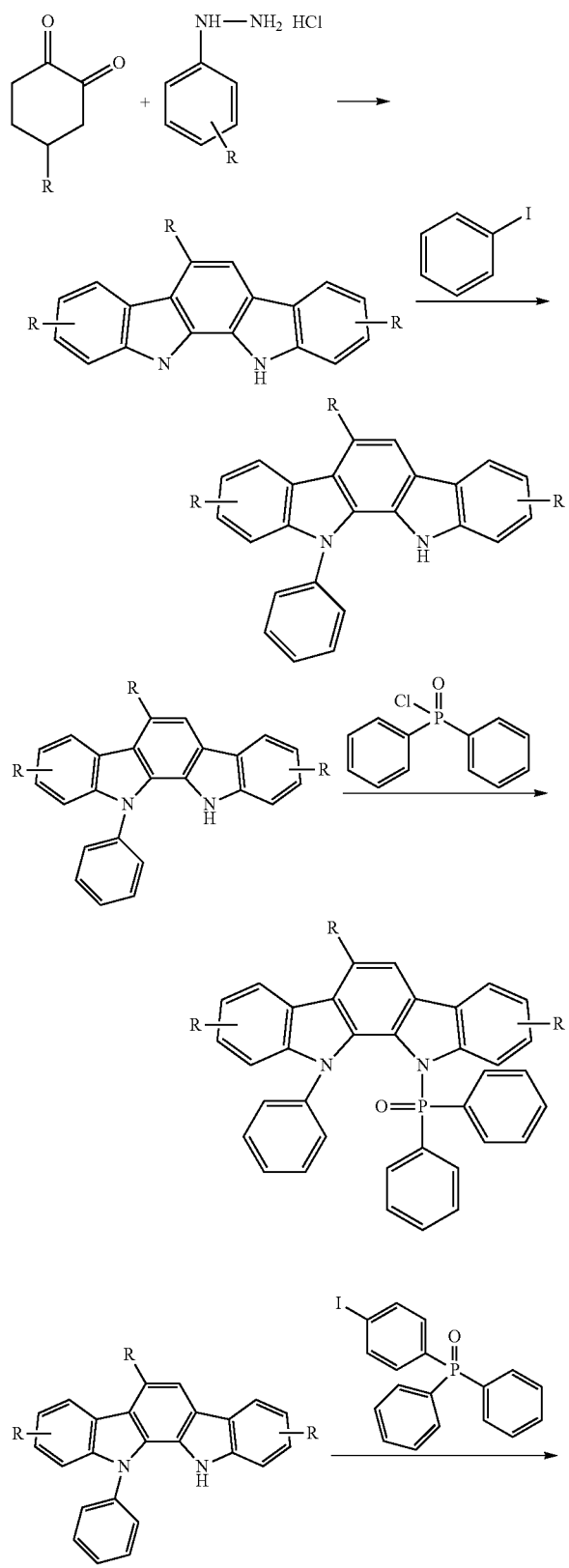

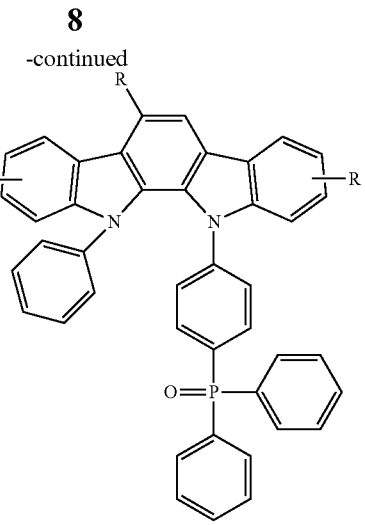

Another method is based on a sequence of reactions illustrated below with reference to a synthetic example described in Archiv der Pharmazie (Weinheim, Germany), 1987, pp. 280-282.

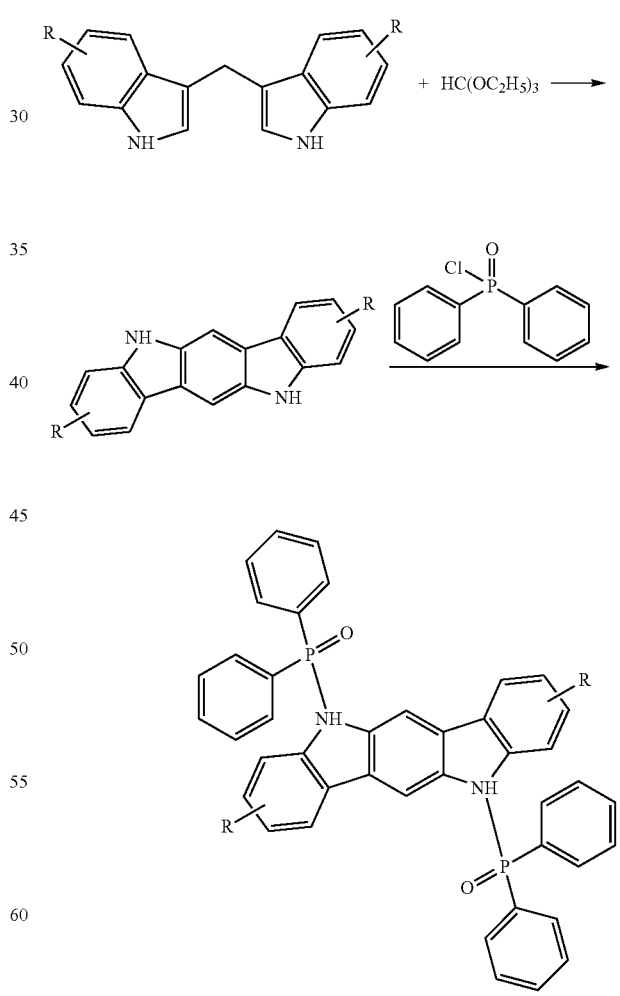

Preferable examples of the compounds represented by general formula (1), (2), or (3) are shown below, but are not limited thereto.

(1)
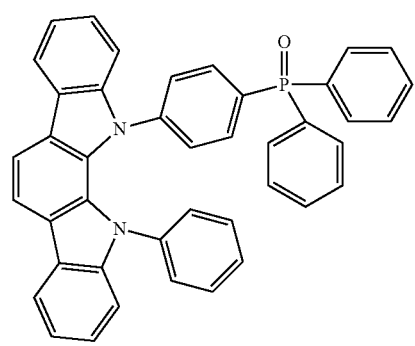
(2)
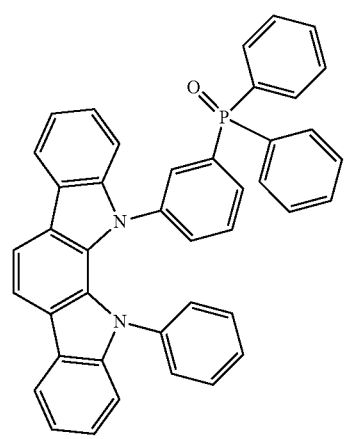
(3)
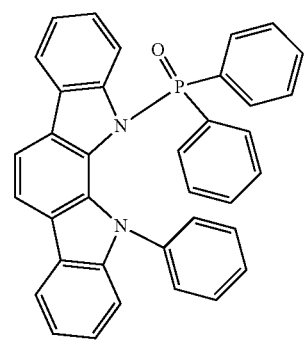
(4)
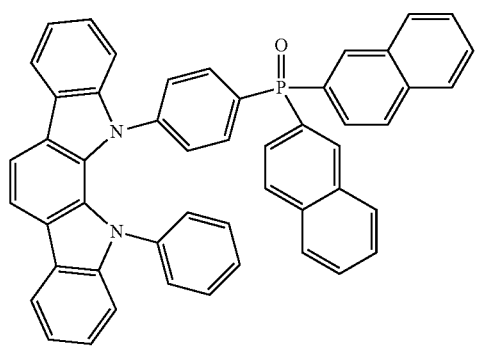
-continued
(5)
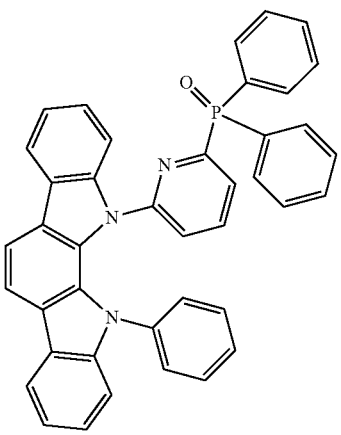
(6)
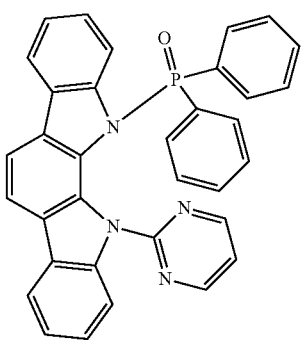
(7)
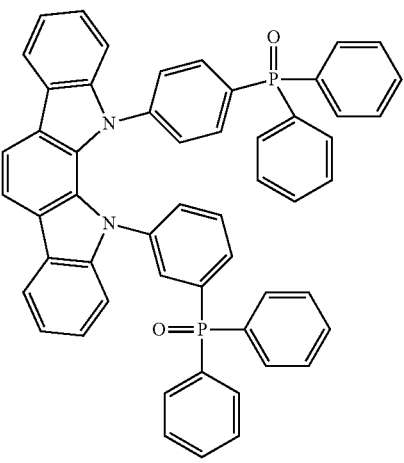
(8)
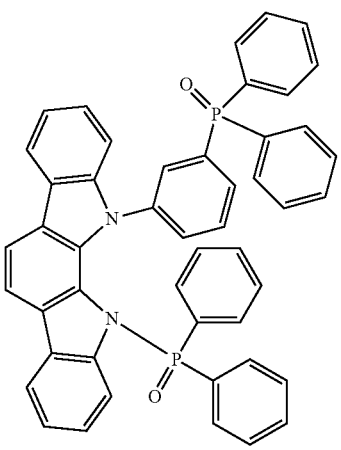

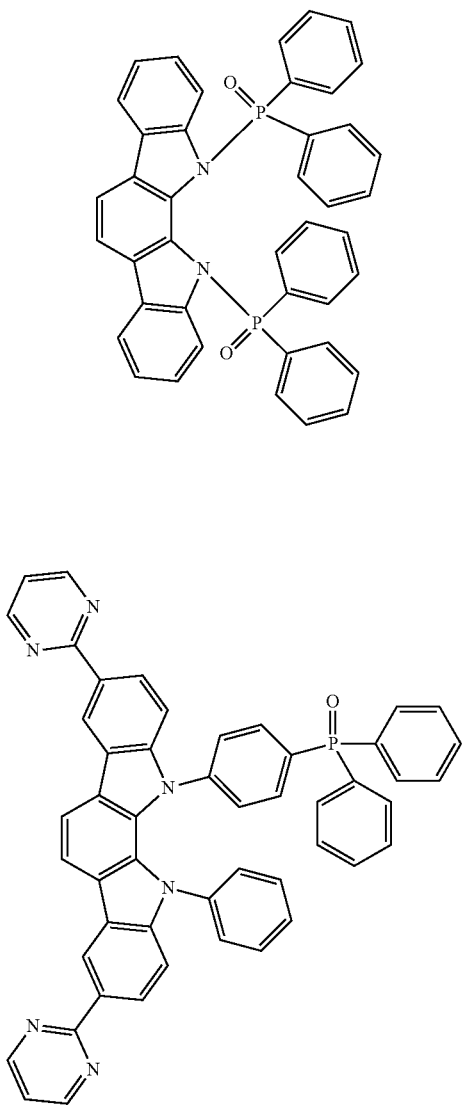
(9)
(11)
(12)
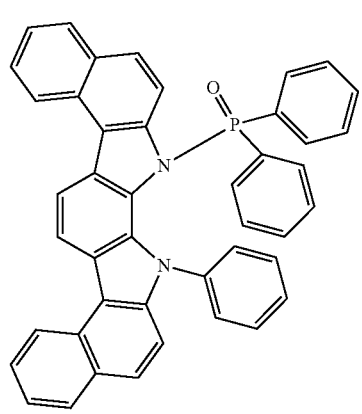
(13)
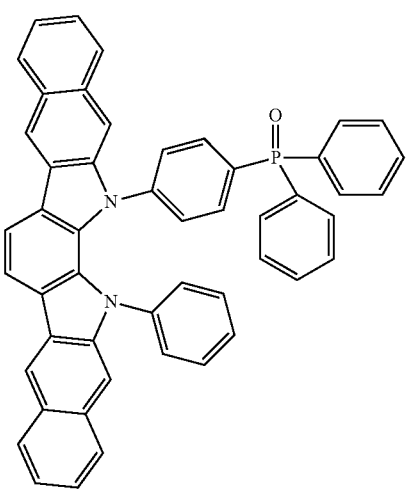
(14)
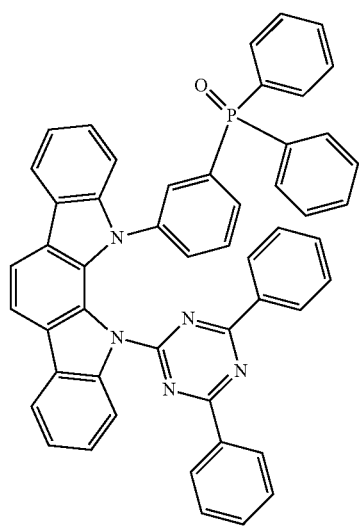
(15)
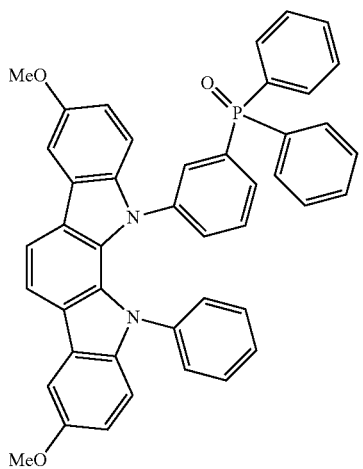

-continued
(16)
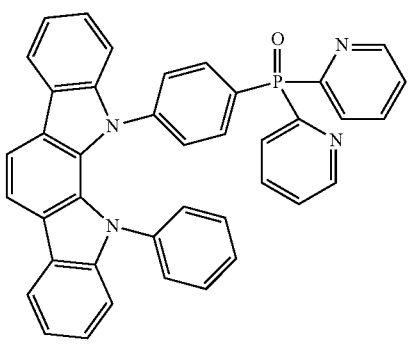
(17)
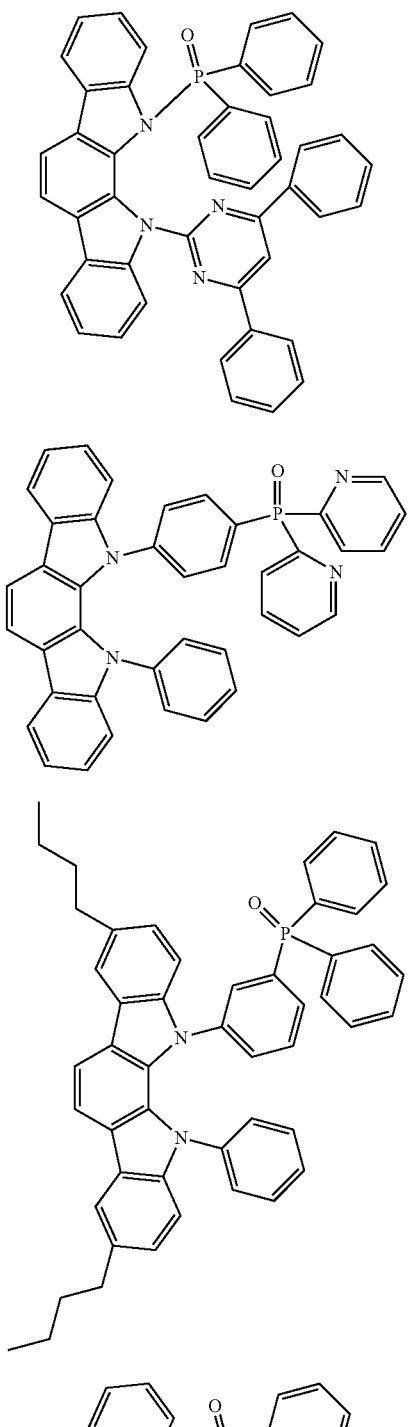
(18)
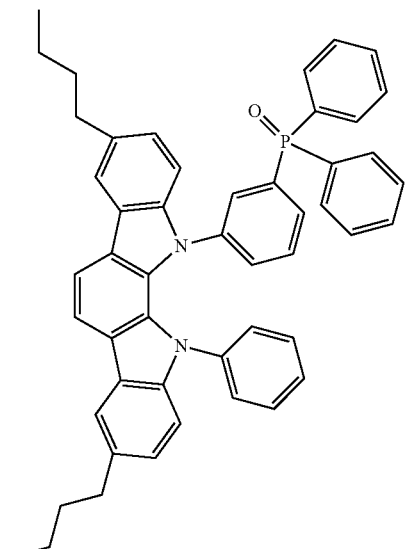
(19)
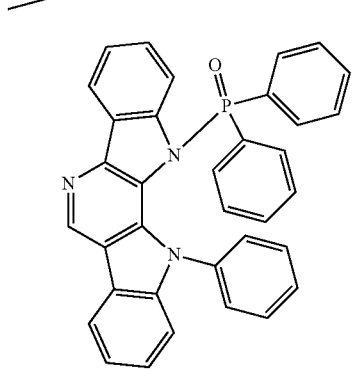
-continued
(20)
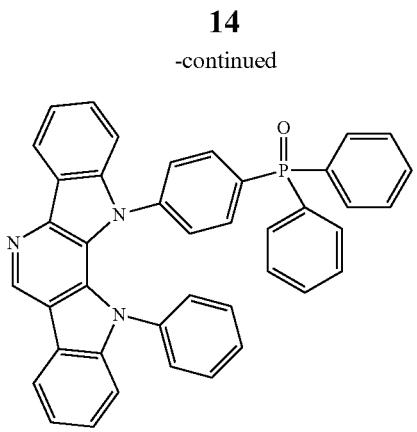
(21)
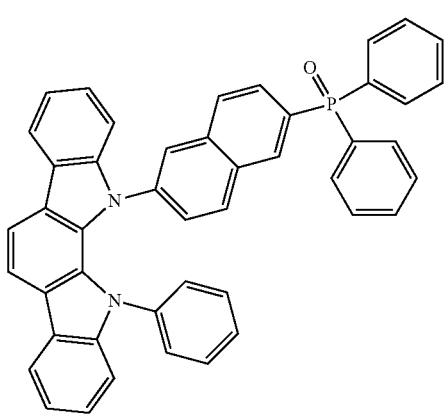
(22)
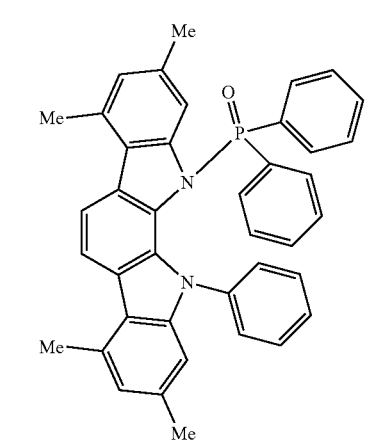
(23)
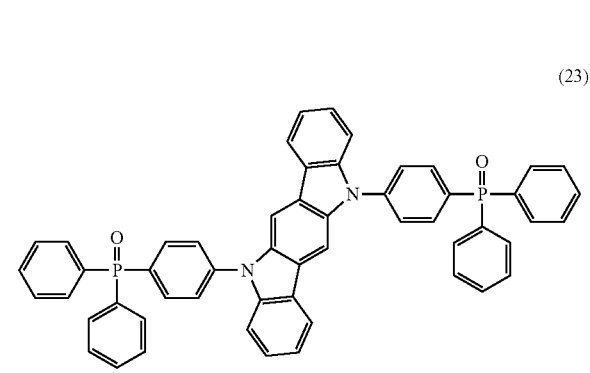

(24)
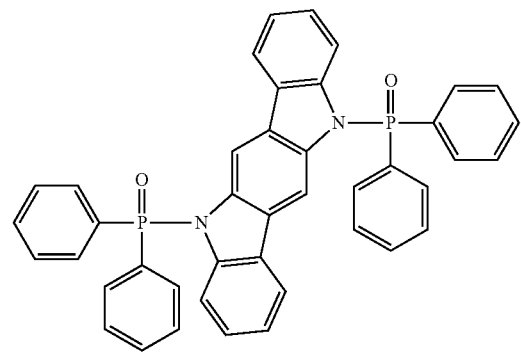
(25)
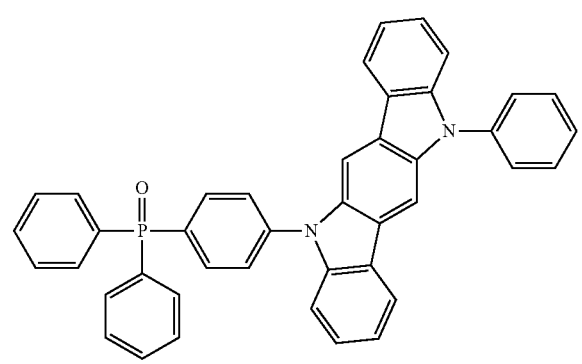
(26)
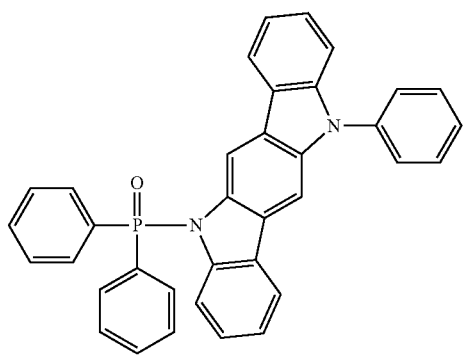
(27)
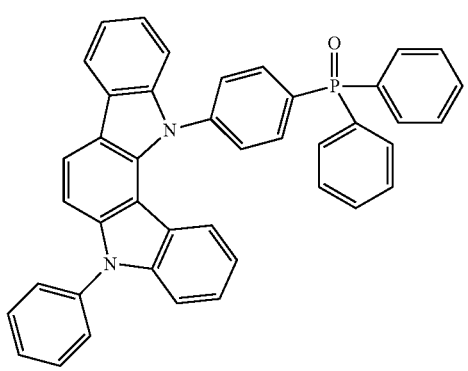
(28)
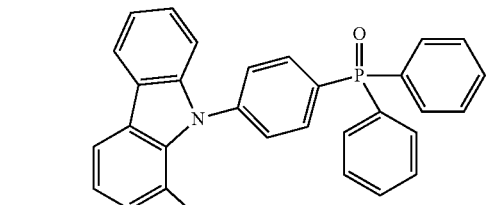
(29)
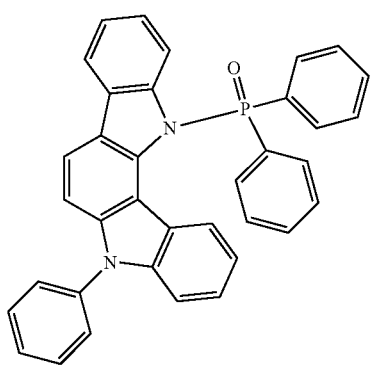
(30)
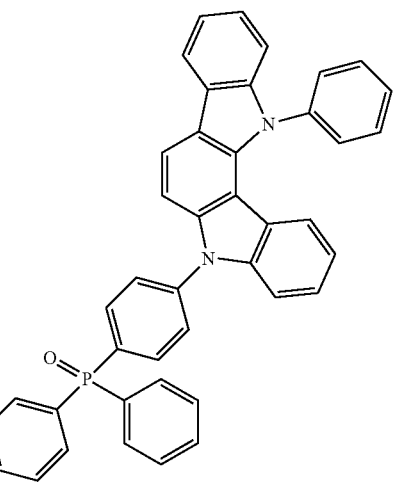
(31)
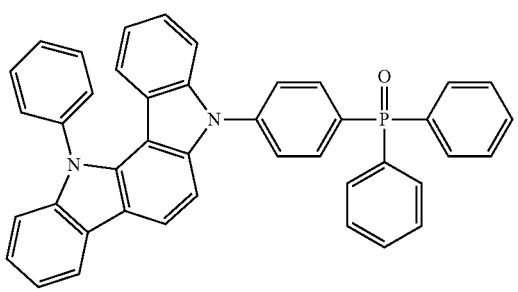

(32)
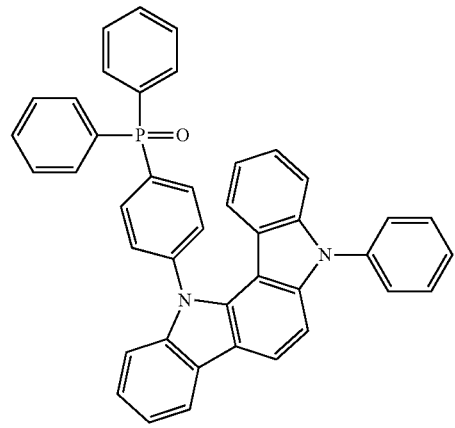
(33)
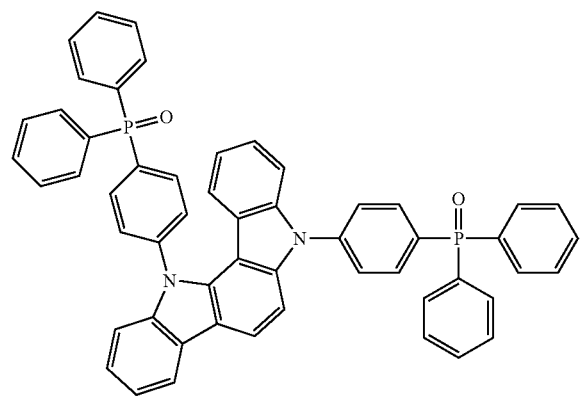
(34)
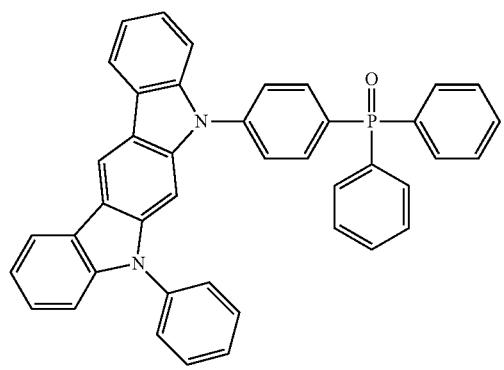
(35)
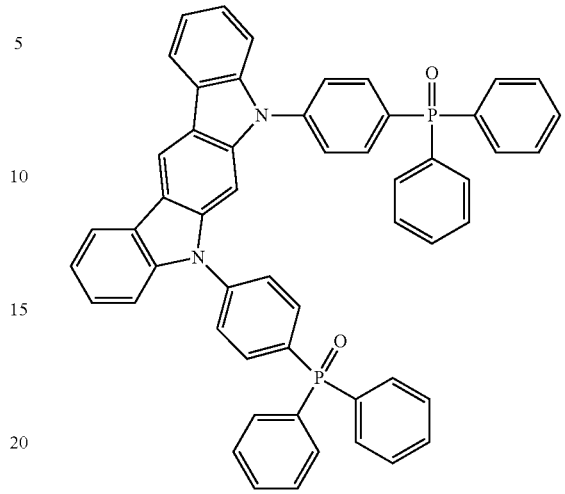
(36)
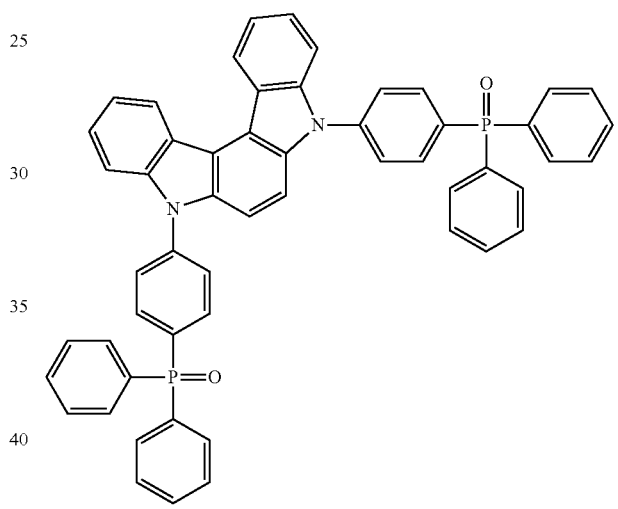
(37)
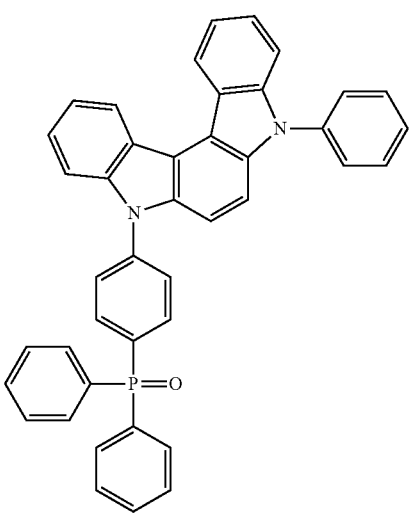

-continued (38)

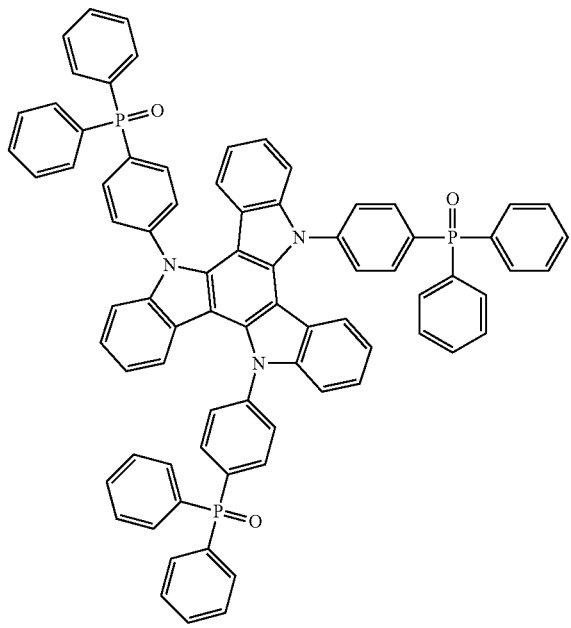

(39)

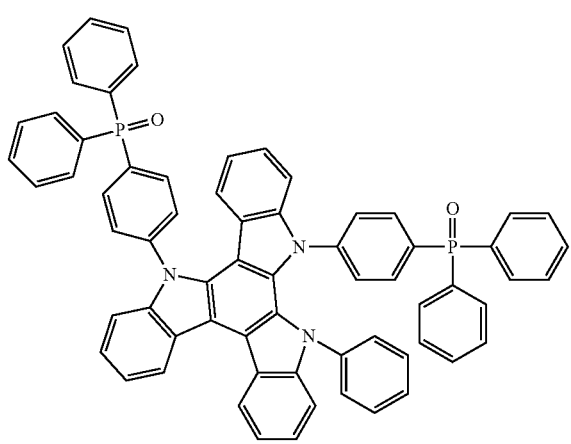

(40)

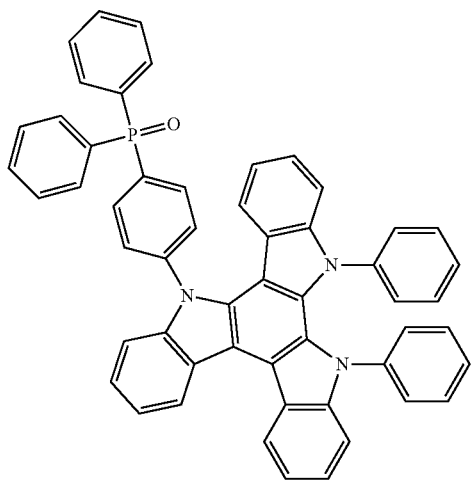

The compound for organic electroluminescent device of this invention provides an excellent organic electroluminescent device when it is incorporated in the organic layer of the device. Advantageously, the compound is incorporated in at least one organic layer selected from a light-emitting layer, a hole-transporting layer, an electron-transporting layer, and a hole-blocking layer. More advantageously, the compound is incorporated as a host material in the light-emitting layer comprising a phosphorescent dopant.

The materials for phosphorescent dopants to be used in the light-emitting layer are preferably organic metal complexes containing at least one metal selected from ruthenium, rhodium, palladium, silver, rhenium, osmium, iridium, platinum, and gold. Such organic metal complexes are well known in the aforementioned patent documents and elsewhere and a suitable complex can be selected from them and used in this invention.

Preferable phosphorescent dopants include complexes containing a noble metal element such as Ir in the center, typically Ir(ppy)3, complexes such as Ir(bt)2·acac3, and complexes such as PtOEt3. Examples of these complexes are shown below, but are not limited thereto.

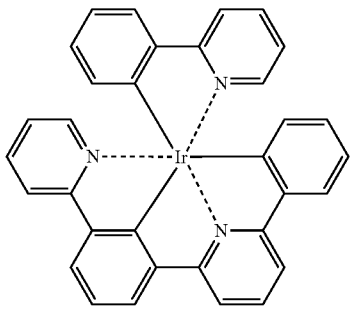

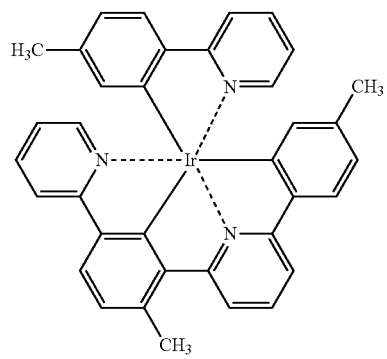

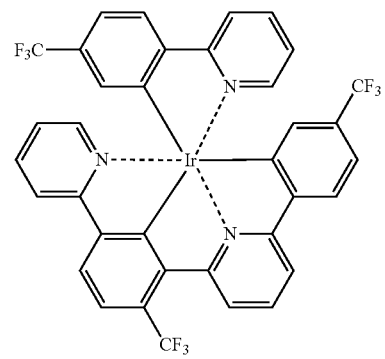

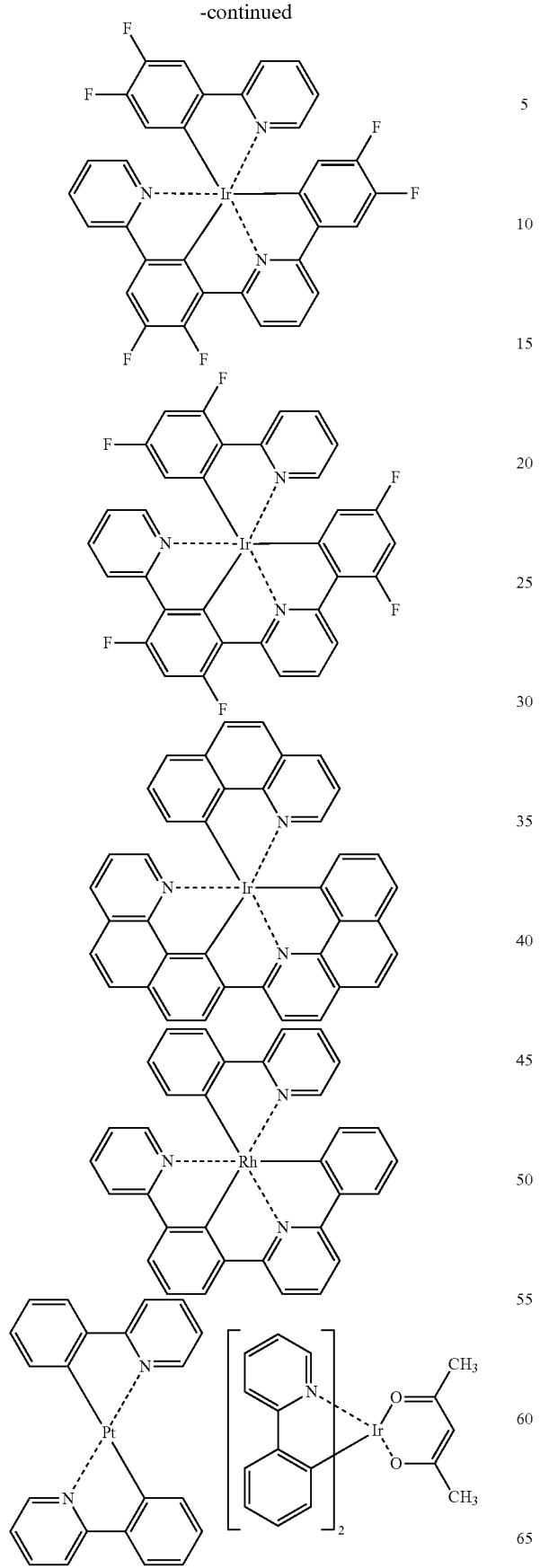

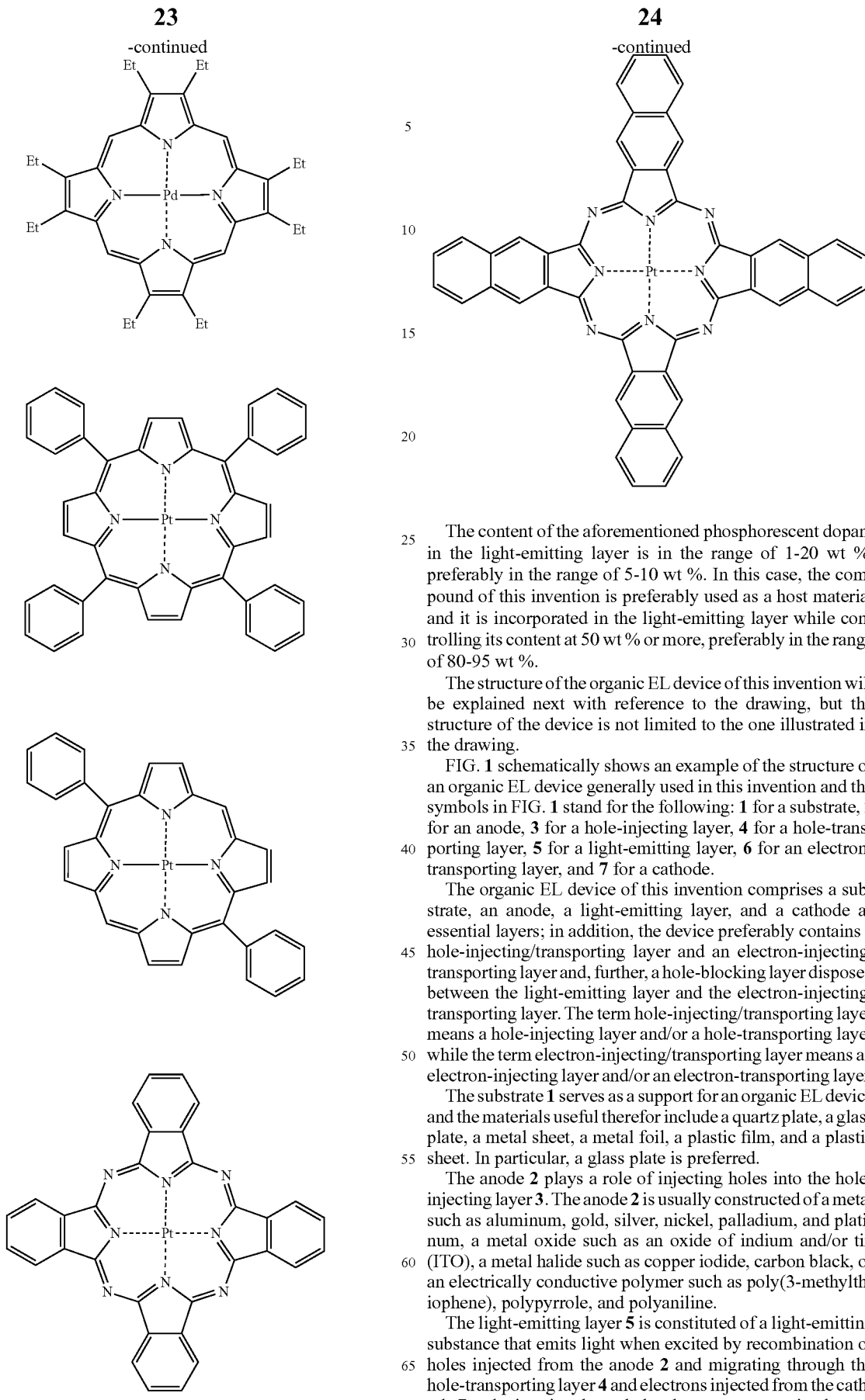

The content of the aforementioned phosphorescent dopant in the light-emitting layer is in the range of 1-20 wt %, preferably in the range of 5-10 wt %. In this case, the compound of this invention is preferably used as a host material and it is incorporated in the light-emitting layer while controlling its content at 50 wt % or more, preferably in the range of 80-95 wt %.

The structure of the organic EL device of this invention will be explained next with reference to the drawing, but the structure of the device is not limited to the one illustrated in the drawing.

FIG. 1 schematically shows an example of the structure of an organic EL device generally used in this invention and the symbols in FIG. 1 stand for the following: 1 for a substrate, 2 for an anode, 3 for a hole-injecting layer, 4 for a hole-transporting layer, 5 for a light-emitting layer, 6 for an electron-transporting layer, and 7 for a cathode.

The organic EL device of this invention comprises a substrate, an anode, a light-emitting layer, and a cathode as essential layers; in addition, the device preferably contains a hole-injecting/transporting layer and an electron-injecting/transporting layer and, further, a hole-blocking layer disposed between the light-emitting layer and the electron-injecting/transporting layer. The term hole-injecting/transporting layer means a hole-injecting layer and/or a hole-transporting layer while the term electron-injecting/transporting layer means an electron-injecting layer and/or an electron-transporting layer.

The substrate 1 serves as a support for an organic EL device and the materials useful therefor include a quartz plate, a glass plate, a metal sheet, a metal foil, a plastic film, and a plastic sheet. In particular, a glass plate is preferred.

The anode 2 plays a role of injecting holes into the hole-injecting layer 3. The anode 2 is usually constructed of a metal such as aluminum, gold, silver, nickel, palladium, and platinum, a metal oxide such as an oxide of indium and/or tin (ITO), a metal halide such as copper iodide, carbon black, or an electrically conductive polymer such as poly(3-methylthiophene), polypyrrole, and polyaniline.

The light-emitting layer 5 is constituted of a light-emitting substance that emits light when excited by recombination of holes injected from the anode 2 and migrating through the hole-transporting layer 4 and electrons injected from the cathode 7 and migrating through the electron-transporting layer 6 upon application of an electrical field to the electrodes. The light-emitting layer 5 preferably comprises a dopant material and a host material consisting of the aforementioned compound for organic EL device as a light-emitting substance.

The cathode 7 plays a role of injecting electrons through the electron-transporting layer 6 into the light-emitting layer 5. The materials useful for the cathode 7 are preferably metals of low work function for efficient injection of electrons and examples include metals such as tin, magnesium, indium, calcium, cesium, aluminum, and silver and alloys thereof. Examples of the alloys include magnesium-silver alloys, magnesium-indium alloys, and aluminum-lithium alloys.

The hole-injecting layer 3, the hole-transporting layer 4, and the electron-transporting layer 6 are optional organic layers; the hole-injecting layer 3 is used for the purpose of enhancing the efficiency of injecting holes into the hole-transporting layer 4 while the hole-transporting layer 4 and the electron-transporting layer 6 transport respectively holes and electrons to the light-emitting layer 5. An electron-injecting layer may be disposed between the cathode 7 and the electron-transporting layer 6. The materials useful for these layers are well known.

The materials for the hole-injecting layer include phthalocyanine compounds such as copper phthalocyanine (CuPC), organic compounds such as polyaniline and polythiophene, and oxides of metals such as vanadium, ruthenium, and molybdenum.

The materials for the hole-transporting layer include triazole derivatives, oxadiazole derivatives, imidazole derivatives, polyarylalkane derivatives, pyrazoline derivatives, pyrazolone derivatives, phenylenediamine derivatives, arylamine derivatives such as NPB, amino-substituted chalcone derivatives, oxazole derivatives, styrylanthracene derivatives, fluorenone derivatives, hydrazone derivatives, stilbene derivatives, silazan derivatives, aniline-based copolymers, and electrically conductive oligomers, typically thiophene oligomers.

The materials for the electron-transporting layer include metal complexes such as Alq3, 10-hydroxybenzo[h]quinoline metal complexes, oxadiazole derivatives, distyrylbiphenyl derivatives, silole derivatives, 3- or 5-hydroxyflavone metal complexes, benzoxazole metal complexes, benzothiazole metal complexes, trisbenzimidazolybenzene, quinoxaline compounds, phenanthroline derivatives, 2-t-butyl-9,10-N,N'-dicyanoanthraquinonediimine, n-type hydrogenated amorphous silicon carbide, n-type zinc sulfide, and n-type zinc selenide.

It is possible to build a structure that is the reverse of the structure shown in FIG. 1 by piling the cathode 7, the electron-transporting layer 6, the light-emitting layer 5, the hole-transporting layer 4, and the anode 2 one upon another in this order on the substrate 1. As described earlier, it is also possible to dispose the organic EL device of this invention between two substrates at least one of which is highly transparent. In this case of the reverse structure, it is possible to add or omit a layer or layers as needed.

The organic EL device of this invention is applicable to a single device, a device with its structure arranged in array, or a device in which the anode and the cathode are arranged in X-Y matrix. This invention provides an organic EL device that is enhanced in the luminous efficiency and markedly improved in the driving stability compared with the conventional devices utilizing emission of light from the excited singlet state by incorporating a compound of a specified skeleton and a phosphorescent dopant in the light-emitting layer and the device can perform excellently in applications to full-color or multicolor panels.

EXAMPLES

This invention will be explained in more detail below with reference to the examples, but it will not be limited to these examples. The compound number in the example corresponds to the number assigned to the chemical formula earlier cited in the specification.

Example 1

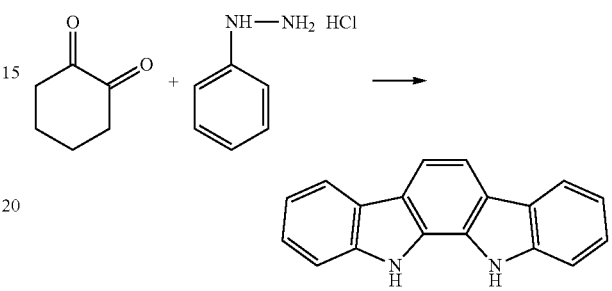

In a nitrogen-blanketed 2,000-ml three-necked flask were placed 33.3 g (297.0 millimoles) of 1,2-cyclohexanedione and 86.0 g (594.7 millimoles) of phenylhydrazine hydrochloride, then 1,000 ml of ethanol was added, and the mixture was stirred. Thereafter, 3.0 g (30.6 millimoles) of concentrated sulfuric acid was added dropwise to the flask over 5 minutes and the resulting mixture was heated to 65° C. and stirred for 4 hours. The mixture was then cooled to room temperature, the purplish brown crystals formed were collected by filtration, and the crystals were reslurried twice in 500 ml of ethanol and then dried under reduced pressure to yield 80.0 g (280.5 millimoles, 96.3% yield) of a purplish brown powder.

In a 1,000-ml three-necked flask was placed 72.0 g (261.5 millimoles) of the aforementioned purplish brown powder, then 720 g of acetic acid and 72.0 g of trifluoroacetic acid were added, and the mixture was stirred. The mixture was then heated to 100° C. and stirred for 15 hours. The mixture was cooled to room temperature, the yellow crystals formed were collected by filtration, and the crystals were rinsed with 200 ml of acetic acid, then rinsed with 200 ml of hexane, and dried under reduced pressure to yield 30.0 g (117.1 millimoles, 44.8% yield) of white powder A'. White powder A' thus obtained is indolo[2,3-a]carbazole.

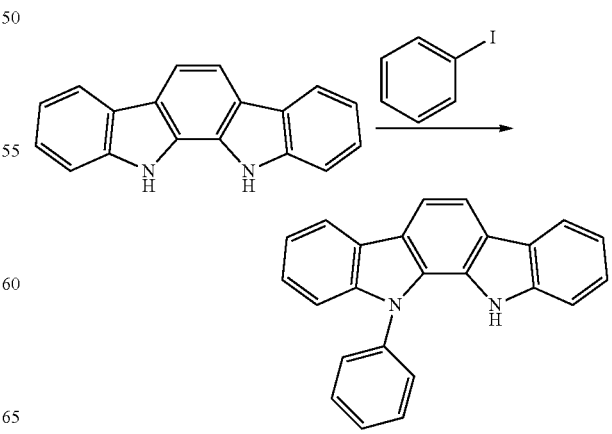

Next, 26.0 g (101.4 millimoles) of the white powder obtained above, 122.7 g (601.4 millimoles) of iodobenzene, 54.7 g (287.2 millimoles) of copper iodide, 66.7 g (482.6 millimoles) of potassium carbonate, and 800 ml of quinoline were placed in a nitrogen-blanketed 1,000-ml three-necked flask and the mixture was stirred. Then, the mixture was heated to 190° C. and stirred for 72 hours. The mixture was cooled to room temperature, 500 ml of water and 500 ml of dichloromethane were added, the mixture was stirred, and the yellow crystals formed were collected by filtration. The filtrate was transferred to a 2,000-ml separatory funnel and separated into an organic layer and an aqueous layer. The organic layer was washed three times with 500 ml of water, dehydrated over magnesium sulfate, the magnesium sulfate was filtered off, and the solvent was distilled off under reduced pressure. The residue was purified by column chromatography to yield 13.7 g (41.2 millimoles, 40.6% yield) of white solid A. White solid A thus obtained is 11-phenylindolo[2,3-a]carbazole.

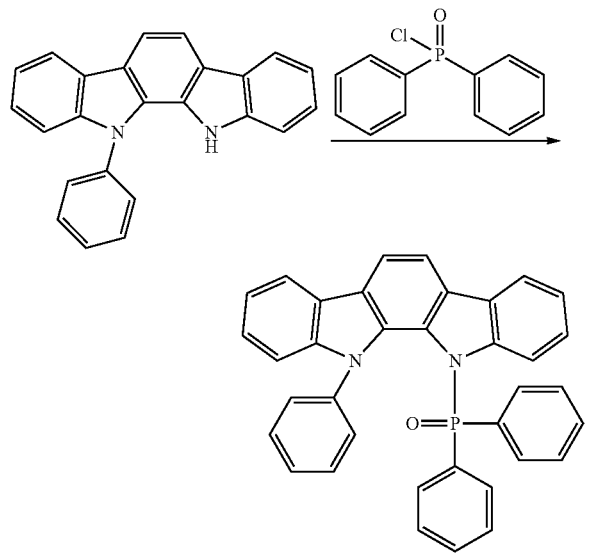

Next, 2.70 g (0.0677 mole) of sodium hydride (60% dispersion) and 80 ml of dehydrated N,N'-dimethylformamide were placed in a nitrogen-blanketed 500-ml three-necked flask and the mixture was stirred under nitrogen flow. A solution of 12.55 g (0.038 mole) of the white powder obtained above in 50 ml of dehydrated N,N'-dimethylformaide was prepared and the solution was added dropwise to the flask over 15 minutes. Upon completion of the dropwise addition, stirring was continued for 1 hour. Then, 15.21 g (0.064 mole) of diphenylphosphinic chloride was thrown in over 15 minutes. Thereafter, stirring was continued for 2 hours. The reaction solution was then added slowly to 1,500 g of stirred water and the crystals separated were collected by filtration. The crystals were reslurried twice in 300 g of water and dried under reduced pressure to yield 16.2 g (0.030 mole, 80.0%) of a slightly yellowish white powder. After drying under reduced pressure, 120 g of chloroform was added, the mixture was stirred for 1 hour, and the crystals were collected by filtration. Thereafter, the organic layer obtained was dehydrated over magnesium sulfate, the magnesium sulfate was filtered off, and the solvent was distilled under reduced pressure. Then, the residue was purified by column chromatography to yield 13.7 g (0.026 mole, 86.7%) of Compound 3 as a white solid.

APCI-MS, m/z 533 [M+H]$^+$; melting point, 258° C.

Example 2

An organic EL device constituted as in FIG. 1 with addition of an electron-injecting layer was fabricated. Applying the vacuum deposition process at a degree of vacuum of $4.0 \times 10^{-4}$ Pa, the constituent layers were deposited in thin film one upon another on a glass substrate on which a 150 nm-thick ITO anode had been formed. First, copper phthalocyanine (CuPC) was deposited on the ITO anode to a thickness of 20 nm as a hole-injecting layer. Then, NPB was deposited to a thickness of 40 nm as a hole-transporting layer. Next, Compound 3 as a host material and Ir(ppy)3 as a dopant were co-deposited from different evaporation sources on the hole-transporting layer to a thickness of 35 nm to form a light-emitting layer. At this point, the concentration of Ir(ppy)3 was 7.0 wt %. After this, Alq3 was deposited to a thickness of 40 nm as an electron-transporting layer. Further, lithium fluoride (LiF) was deposited on the electron-transporting layer to a thickness of 0.5 nm as an electron-injecting layer. Finally, aluminum (Al) as an electrode was deposited on the electron-injecting layer to a thickness of 170 nm to complete the fabrication of the organic EL device.

The organic EL device thus fabricated was connected to an outside power source and, when direct current voltage was applied, the device was confirmed to emit light with the characteristics shown in Table 1. In Table 1, the luminance, voltage, and luminous efficiency were measured at 10 mA/cm$^2$. The maximum wavelength of the spectrum of light emitted from the device was 517 nm and this proves that light is emitted from Ir(ppy)3.

Comparative Example 1

An organic EL device was fabricated as in Example 2 with the exception of using HMTPD in the hole-transporting layer and TAZ as a host material in the light-emitting layer. In Table 1, the luminance, voltage, and luminous efficiency were measured at 10 mA/cm$^2$. The maximum wavelength of the spectrum of light emitted from the device was 517 nm and this proves that light is emitted from Ir(ppy)3.

Comparative Example 2

An organic EL device was fabricated as in Example 2 with the exception of using TAZ as a host material in the light-emitting layer. The maximum wavelength of the spectrum of light emitted from the device was 517 nm and this proves that light is emitted from Ir(ppy)3.

TABLE 1

| | Compound No. | Luminance (cd/m$^2$) | Voltage (V) | Luminous efficiency (lm/W) |
|---|---|---|---|---|
| Example 2 | 3 | 2800 | 4.4 | 20.0 |
| Comparative example 1 | — | 2050 | 13.2 | 4.9 |
| 2 | — | 1270 | 9.5 | 4.2 |

INDUSTRIAL APPLICABILITY

The organic EL device of this invention is capable of emitting light of high luminance at high efficiency with application of low voltage. Hence, the device is of high technical value because of its potential applicability to flat panel displays (for example, in office computers and wall-hanging television sets), vehicle-mounted display devices, mobile phone displays, light sources utilizing the characteristics of planar light emitters (for example, light sources for copiers and backlight sources of liquid crystal displays and instruments), signboards, and beacon lights.

The invention claimed is:

1. A compound for organic electroluminescent device represented by the following general formula (1):

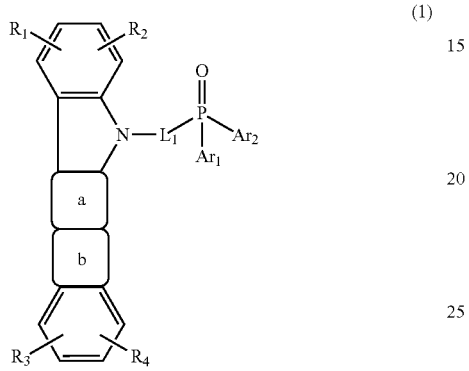

(1)

wherein ring a is an aromatic or heterocyclic ring fused to two adjacent rings and represented by formula (a1) or (a2),
ring a' is an aromatic or heterocyclic ring fused to three adjacent rings and represented by formula (a1), and
ring b is a heterocyclic ring fused to two adjacent rings and represented by formula (b1);

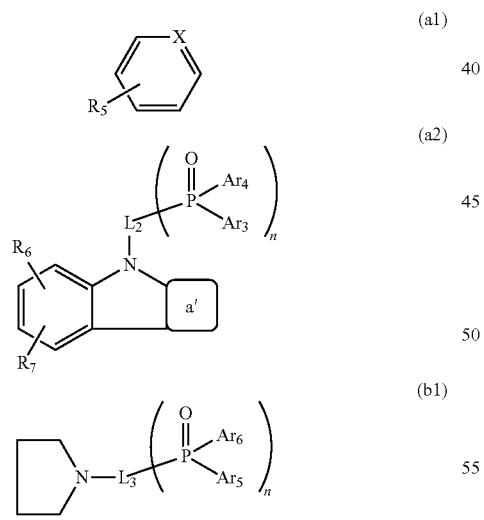

X is independently CR or N;
$Ar_1$ to $Ar_6$ each is independently a substituted or unsubstituted aromatic hydrocarbon or aromatic heterocyclic group;
R and $R_1$ to $R_7$ each is independently hydrogen, an alkyl group, an aralkyl group, an alkenyl group, an alkynyl group, a cyano group, a dialkylamino group, a diarylamino group, diaralkylamino group, an amino group, a nitro group, an acyl group, an alkoxycarbonyl group, a carboxyl group, an alkoxy group, an alkylsulfonyl group, a haloalkyl group, a hydroxyl group, an amide group, or a substituted or unsubstituted aromatic hydrocarbon or aromatic heterocyclic group, and in the case where any two of the foregoing are located adjacent to each other, R and $R_1$ to $R_7$ are optionally linked to form a fused ring;
$L_1$ to $L_3$ each is independently a direct bond or a linking group constituted of a substituted or unsubstituted aromatic heterocyclic group; and
n is independently an integer of 0 or 1.

2. The compound for organic electroluminescent device as described in claim 1, wherein the compound is represented by the following general formula (2):

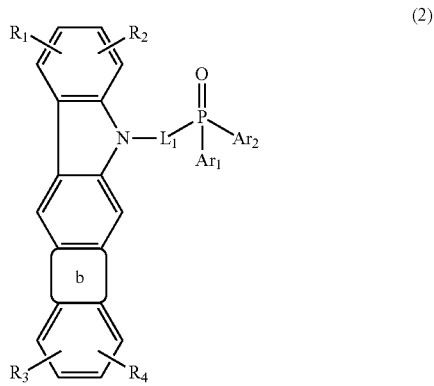

(2)

wherein ring b, $Ar_1$, $Ar_2$, $R_1$ to $R_4$, and $L_1$ of formula (2) have the same meanings as ring b, $Ar_1$, $Ar_2$, $R_1$ to $R_4$, and $L_1$, respectively, of general formula (1).

3. The compound for organic electroluminescent device as described in claim 1, wherein the compound is represented by the following general formula (3):

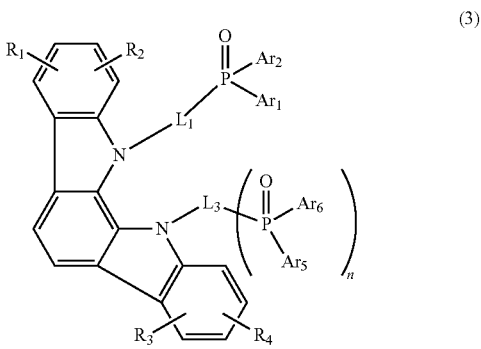

(3)

wherein $Ar_1$, $Ar_2$, $A_5$, $A_6$, $R_1$ to $R_4$, $L_1$, $L_3$, and n of formula (3) have the same meanings as $Ar_1$, $Ar_2$, $A_5$, $A_6$, $R_1$ to $R_4$, $L_1$, $L_3$, and n, respectively, of general formula (1).

4. The compound for organic electroluminescent device as described in claim 1, wherein, in general formula (1), $Ar_1$ to $Ar_6$ each is independently a substituted or unsubstituted phenyl group or a substituted or unsubstituted aromatic heterocyclic group of 2 to 5 carbon atoms.

5. The compound for organic electroluminescent device as described in claim 1, wherein, in general formula (1), $R_1$ to $R_5$ each is independently hydrogen, a substituted or unsubstituted aromatic hydrocarbon group of 5 to 18 carbon atoms, or a substituted or unsubstituted aromatic heterocyclic group of 3 to 17 carbon atoms.

6. An organic electroluminescent device comprising the compound for organic electroluminescent device described in any one of claims 1 to 5.

7. The organic electroluminescent device as described in claim 6, wherein an organic layer comprising a compound for organic electroluminescent device is at least one layer selected from the group consisting of a light-emitting layer, a hole-transporting layer, a hole-injecting layer, an electron-transporting layer, an electron-injecting layer, and a hole-blocking layer.

8. The organic electroluminescent device as described in claim 6, wherein the organic layer comprising a compound for organic electroluminescent device is a light-emitting layer and the said light-emitting layer comprises a phosphorescent dopant and the said compound for organic electroluminescent device as a host material.

* * * * *